United States Patent [19]

Hashimoto et al.

[11] Patent Number: 4,885,168

[45] Date of Patent: Dec. 5, 1989

[54] METHOD FOR THE REMOVAL OF NUCLEIC ACIDS AND/OR ENDOTOXIN

[75] Inventors: Masanori Hashimoto, Yamato; Takeshi Yamamoto, Takatsuki; Toru Kawachi, Yamato; Junji Kuwashima, Toyonaka; Hirokazu Kitaoka, Hirakata, all of Japan

[73] Assignees: Dainippon Pharmaceutical Co., Ltd., Osaka; Kurita Water Industries Ltd., Tokyo, both of Japan

[21] Appl. No.: 34,217

[22] Filed: Apr. 1, 1987

[30] Foreign Application Priority Data

Apr. 2, 1986 [JP] Japan .................................. 61-75779

[51] Int. Cl.$^4$ ............................................ A61K 35/00
[52] U.S. Cl. ............................................ 424/95; 514/2; 210/720; 536/20
[58] Field of Search ................. 514/55, 974; 530/412, 530/418, 419, 421, 812, 813, 814, 821, 825; 536/20; 424/95

[56] References Cited

U.S. PATENT DOCUMENTS

| | | | |
|---|---|---|---|
| 3,922,260 | 11/1975 | Peniston et al. | 536/20 |
| 4,474,769 | 10/1984 | Smith | 514/55 |
| 4,605,623 | 8/1986 | Malette et al. | 514/55 |
| 4,726,947 | 2/1988 | Shimada et al. | 424/92 |

Primary Examiner—Ronald W. Griffin
Assistant Examiner—Jean C. Witz
Attorney, Agent, or Firm—Scully, Scott, Murphy & Presser

[57] ABSTRACT

Agent for the removal of nucleic acids and/or endotoxin from a liquid containing the nucleic acids and/or endotoxin and further useful substances (e.g. proteins, hormones, etc.), which comprises as an active ingredient a chitosan having a low molecular weight, particularly that having an intrinsic viscosity of 0.01 to 5 (dl/g) and further a colloid equivalent of not less than 2 meq/g of evaporated residue.

7 Claims, No Drawings

METHOD FOR THE REMOVAL OF NUCLEIC ACIDS AND/OR ENDOTOXIN

This invention relates to an agent for the removal of nucleic acids (DNA, RNA) and/or endotoxin from a liquid containing nucleic acids and/or endotoxin, particularly from a liquid containing nucleic acids, endotoxin and proteins, and a method for the removal of nucleic acids and/or endotoxin from the liquid. More particularly, it relates to an agent which comprises as an active ingredient a chitosan having a low molecular weight (hereinafter, it may optionally be referred to as "low molecular chitosan" or "low mol. chitosan"), which is useful for the removal of nucleic acids and/or endotoxin from a liquid containing nucleic acids and/or endotoxin and further proteins, particularly proteins having an isoelectric point of not less than 3, such as anti-tumor substances originated from human cells, immune system regulation factors, proteins from human blood or tissues, hormones, and other enzymes and physiologically active peptides originated from various microorganisms or cells.

PRIOR ART

It has been known that various physiologically active substances and various useful substances (e.g. proteins, enzymes, etc.) in cells are produced and isolated by culturing various microorganisms or cells of human, animal or plant tissues. Besides, with recent progress in biotechnology, these useful substances have practically been produced on large scale by gene engineering technique, i.e. by culturing microorganisms which are transformed with an expression vector in which a gene encoding the physiologically active substances, proteins or hormones is inserted. In both techniques, the cells obtained by the culture are disrupted by mechanical or ultrasonic treatment, by which the cell walls and cell membranes are broken, and then, cell debris are removed by centrifugation or other means to give cell extract. After removing impurities such as nucleic acids in the cell extract, the extract is subjected to a conventional purification method such as chromatography to obtain the desired purified substances.

The separation of the useful protein substances from the impurities such as nucleic acids in the cell extract has usually been carried out, for example, by a method of precipitating the useful protein substances by adjusting pH of the extract to acidic region (e.g. pH 4.1 to 4.8) with an acid such as hydrochloric acid [cf. Japanese Patent First Publication (Kokai) No. 12496/1978]; by a method of salting out with ammonium sulfate [cf. British Patent Publication No. 1,286,014]; by a method of precipitating with a polyvalent metallic salt, etc. [cf. Japanese Patent First Publication (Kokai) No. 114290/1980]; by a method of precipitating nucleic acids with protamine sulfate or streptomycin sulfate [cf. Japanese Patent First Publication (Kokai) No. 114290/1980, and Seikagaku Jikken Koza (Series of Biochemical Experiments), Vol. 5, pages 200–201]; or a method of precipitating nucleic acids with polyethyleneimine [European Patent Publication No. 60465, and Japanese Patent First Publication (Kokai) No. 152478/1983].

When the useful substances contained in the above extract are used as a medicament which is directly administered to human body, it is essential to remove endotoxin therefrom. Endotoxin is also called as intracellular toxin. Particularly, the endotoxin originated from gram negative bacteria (e.g. *Escherichia coli*) is severe pyrogen, and when it is injected into human body, it induces a chill or a fever. Accordingly, it has been desired to develop an excellent method for the effective removal of the endotoxin.

There are known some methods for the removal of endotoxin using an oxidizing agent [cf. Japanese Patent First Publication (Kokai) No. 63924/1981], with heating [cf. Japanese Patent First Publication (Kokai) No. 51245/1979], using an active carbon [cf. Japanese Patent First Publication (Kokai) No. 36887/1977], using an ion exchange resin [cf. Japanese Patent First Publication (Kokai) No. 57314/1977], using a synthetic adsorbent [cf. British Pat. Nos. 1,418,286 and 2,092,470], using an ultrafiltration membrane [cf. Japanese Patent Publication (Kokoku) No. 28156/1981], using a reverse osmosis membrane [cf. Japanese Patent First Publication (Kokai) No. 64948/1978], and the like. There is also known a method comprising adding an aluminum salt or a zinc salt to a liquid containing proteins and endotoxin to precipitate the proteins and to remain endotoxin in the supernatant [cf. Japanese Patent First Publication (Kokai) No. 35521/1982].

However, among the above known methods for the removal of nucleic acids, etc., according to the method of treating the cell extract at a low pH range, the method using ammonium sulfate, or the method using a polyvalent metallic salt, the useful protein substances are precipitated, and hence, it is necessary to re-dissolve the precipitate in order to purify the useful substances, in which the separation is unsatisfactorily effective. The method of salting out with ammonium sulfate requires troublesome step of dialysis. Moreover, the methods using protamine sulfate or streptomycin sulfate are not suitable for the separation on an industrial scale because of using expensive reagents which is not economical, and further they have a problem in possibility of contamination of other proteins and of remaining of antibiotics. The method of precipitating nucleic acids with polyethyleneimine is fairly effective for the removal of nucleic acids, but there is still a problem of possibility of remaining of harmful decomposed products of the polyethyleneimine.

Besides, among the above known methods for the removal of endotoxin, the method using an oxidizing agent or with heating results in denaturing or inactivation of the useful substances even though endotoxin may be well removed. The adsorbing method can not give sufficient separation of endotoxin from the useful substances. The methods using membranes can not be used for the separation of endotoxin having a molecular weight of one million or more from the useful substances having a high molecular weight and further have a problem in the high cost for the apparatus and maintenance thereof. Moreover, in the method using an aluminum salt and a zinc salt, the proteins are to be precipitated in order to separate pyrogens, and hence, the proteins must be re-dissolved in order to further purify them.

BRIEF DESCRIPTION OF THE INVENTION

In view of various problems in the known methods, the present inventors have extensively studied an improved method for the removal of nucleic acids and/or endotoxin with high efficiency by simple and safe means, and have found that a specific low molecular chitosan is effective for the removal of nucleic acids and/or endotoxin from a liquid containing them and other useful substances.

An object of the invention is to provide an improved agent for the removal of nucleic acids and/or endotoxin, which comprises as an active ingredient a low molecular chitosan. Another object of the invention is to provide a method for the removal of nucleic acids and/or endotoxin from a liquid containing them and other useful substances by using a low molecular chitosan. These and other objects and advantages of the invention will be apparent to those skilled in the art from the following description.

DETAILED DESCRIPTION OF THE INVENTION

The low molecular chitosan used in this invention is prepared by depolymerizing a chitosan having a high molecular weight which is derived from natural chitin and has an intrinsic viscosity of 0.01 to 5 (dl/g), preferably 0.03 to 2 (dl/g), more preferably 0.2 to 1 (dl/g). When the intrinsic viscosity of the chitosan is less than 0.01 (dl/g) or more than 5 (dl/g), they are inferior in the efficiency of the removal of nucleic acids and endotoxin. The low molecular chitosan has preferably a colloid equivalent (charge density) of not less than 2 meq/g of evaporated residue, more preferably not less than 4 meq/g of evaporated residue. When the colloid equivalent of the low molecular chitosan is less than 2 meq/g of evaporated residue, the low molecular chitosan must unfavorably be used in a larger amount.

The starting material for preparing the low molecular chitosan is a chitosan having a high molecular weight which is prepared by isolating chitin from exoskeletons of crabs, shrimps, lobsters, etc. and deacetylating the chitin with an alkali. The chitosan having a high molecular weight thus prepared is treated with hydrogen peroxide, nitrite ion, alkali, acid or the like, by which the glucoside bond is cleaved to give the desired low molecular chitosan. Various depolymerization methods of a chitosan are known, for example, a method of depolymerization by treating the chitosan with sodium nitrite [cf. U. S. Pat. No. 3,922,260]; a method of depolymerization with hydrogen peroxide [cf. Japanese Patent First Publication (Kokai) No. 148890/1979]; a method of depolymerization with chlorine gas [cf. Japanese Patent First Publication (Kokai) No. 186504/1980]; and a method of polymerization with sodium perborate [cf. Japanese Patent First Publication (Kokai) No. 40303/1986]. The chitosan depolymerized by any of these and other known methods may be used in this invention, but for the purpose of effectively removing nucleic acids and/or endotoxin of this invention, the cleavage with hydrogen peroxide is particularly favorable because the colloid equivalent of the chitosan is little decreased. By controlling the concentration of hydrogen peroxide, there can be obtained the desired low molecular chitosan having an optional intrinsic viscosity. The favorable method comprises suspending the starting chitosan having a high molecular weight in an alkali solution, adding thereto an appropriate concentration of hydrogen peroxide, subjecting to the cleavage at constant temperatures for a certain period of time, removing water by filteration, and then drying. Preferred cleavage conditions are pH 6-12, a concentration of hydrogen peroxide of 0.005 to 10% by weight, a liquid temperature of 20° to 90° C., and a reaction period of 30 to 500 minutes.

The agent for the removal of nucleic acids and/or endotoxin of this invention contains as the active ingredient the low molecular chitosan as mentioned above, but may optionally contain other ingredients, such as natural or synthetic precipitating agent, precipitation auxiliary, and the like.

The materials to be removed are nucleic acids (DNA, RNA) and/or endotoxin and both of nucleic acids and endotoxin may simultaneously or separately be removed. The term "removal" in this invention means removing off (elimination) and/or separation of nucleic acids and/or endotoxin from the liquid to be treated. The liquid to be treated may contain these nucleic acids and/or endotoxin as an impurity, or may contain them as a useful substance. In case of containing the nucleic acids and/or endotoxin as an impurity, the useful substances are separated and purified by removing off these nucleic acids and/or endotoxin. In case of containing these nucleic acids and/or endotoxin as a useful substance, these are separated and purified from the liquid to be treated.

In the method of the removal of nucleic acids and/or endotoxin of this invention, the liquid to be treated is not specified but includes various liquids containing the nucleic acids and/or endotoxin. The liquid to be treated which contains nucleic acids and/or endotoxin is for example a liquid containing nucleic acids and/or endotoxin as well as specific proteins as a useful substance. In this case, the liquid is subjected to the method of this invention, by which the nucleic acids and/or endotoxin are removed off and the desired useful protein substances are purified and recovered.

The useful protein substances include water soluble proteins or protein-like materials having an isoelectric point of not less than 3, for example, anti-tumor substances originated from human cells, such as interferon, tumor necrosis factor (abbreviated as "TNF"), lymphotoxin, interleukin, etc.; immune system regulation factors, such as colony stimulating factor, macrophage activating factor, etc.; proteins originated from human blood or tissues, such as albumin, $\gamma$-globulin, urokinase, tissue plasminogen activator, superoxide desmutase, erythropoetin, etc.; hormones, such as insulin, growth hormones, somatostatin, etc.; and other enzymes and physiologically active peptides originated from various microorganisms or cells. These proteins include also any new substances which will newly be isolated in future.

The liquid to be treated which contains the proteins or protein-like materials as mentioned above includes, for example, various extracts obtained by disrupting cells of various microorganisms, human or other animal tissues or plant tissues or culture broth of these microorganisms or cell culture medium. The liquid to be treated includes also a liquid used for the preparation of medicaments. That is, the impurities such as endotoxin are removed off from the liquid, and the highly purified liquid is used as a liquid for injections, etc.

The agent for the removal of nucleic acids and/or endotoxin of this invention is useful for the removal of nucleic acids and/or endotoxin from various liquids mentioned above. The removal method of nucleic acids and/or endotoxin comprises adding the removal agent of this invention to the liquid to be treated, and separating off the precipitate by a conventional solid-liquid separation method. In this method, the nucleic acids and/or endotoxin are bound with the low molecular chitosan to form an insoluble precipitate, and hence, they are easily be removed by a conventional solid-liquid separation method.

The removal agent of this invention is preferably used in the form of an aqueous solution having a concentration of the low molecular chitosan of 1 to 10% by weight, but may be used in the form of a powder. Alternatively, the removal method may be carried out by filling the low molecular chitosan which is adsorbed onto an adsorbent in a column, and therethrough passing a liquid to be treated, whereby dissolving gradually the low molecular chitosan and precipitating nucleic acids and/or endotoxin; or by fixing the low molecular chitosan onto a carrier and therethrough passing a liquid to be treated, whereby adsorbing nucleic acids and/or endotoxin onto the carrier. The most suitable method may optionally be selected in accordance with each liquid to be treated.

As to a specific protein-containing cell extract, the method for the removal of nucleic acids and/or endotoxin of this invention is more specifically explained below, but the removal method can also be applied to the liquids to be treated mentioned above likewise.

The low molecular chitosan is added to a protein-containing cell extract and the mixture is stirred, by which nucleic acids and/or endotoxin are precipitated together with the low molecular chitosan, and the mixture containing a precipitate is subjected to a solid-liquid separation by a conventional method in order to separate the nucleic acids and/or endotoxin from the proteins. In the above procedure, the cell extract has preferably a pH only a little higher than the isoelectric point of the proteins after being added with the low molecular chitosan, but not higher than pH 8. When the extract has higher than pH 8, the removal efficiency of the nucleic acids and/or endotoxin is unfavorably decreased. The temperature of the liquid to be treated is not specified, but it is preferably controlled in the range of 0° to 5° C. during the procedure. The low molecular chitosan is usually added in an amount of 50 to 200% by weight based on the weight of the nucleic acids (DNA and RNA). Besides, when an inorganic or organic salt is copresent in higher concentration in the liquid to be treated, the salt affects on the removal of nucleic acids and/or endotoxin. For example, when the liquid to be treated contains sodium chloride in a concentration of 0.5 M or more, the removal efficiency of nucleic acids and/or endotoxin is significantly decreased. Thus, the liquid to be treated has preferably a concentration of salts as low as possible.

According to the above method, when the low molecular chitosan is added to the liquid to be treated, the nucleic acids and/or endotoxin and other impurities are bound with the low molecular chitosan to form insoluble materials and then precipitate. The specific proteins to be purified remain in the supernatant and hence are easily separated from the impurities. The specific proteins thus separated are optionally subjected to further purification step by a conventional method. The nucleic acids and/or endotoxin adsorbed onto the low molecular chitosan may also be isolated and recovered as a useful substance by a conventional method.

In the above method, if the chitosan having a high molecular weight prepared from natural chitin is used instead of the low molecular chitosan, the desired removal efficiency is hardly observed, because when the chitosan having a high molecular weight [which has an intrinsic viscosity of about 13 (dl/g)] is dissolved in a dilute acid, the solution becomes a viscous cationic colloidal solution, and hence it is difficult to prepare a high concentration of chitosan solution, and also because the solution of chitosan must be added in an amount almost equal to the volume of the liquid to be treated in order to exhibit the desired removal efficiency though the colloid equivalent is about 5 meq/g of evaporated residue, and hence, it is not practically used in view of difficulty in procedure and also in economical viewpoint. On the contrary, when the low molecular chitosan prepared by chemically modifying the chitosan having a high molecular weight is used, it is possible to prepare a solution containing the chitosan in a high concentration, and the solution can give high removal efficiency for nucleic acids and/or endotoxin. Thus, the low molecular chitosan as used in this invention can be used in a very small amount for effective removal of nucleic acids and/or endotoxin. Accordingly, even in case of a cell extract which contains a large amount of impurities such as nucleic acids and/or endotoxin, the method of this invention can be used for the simultaneous removal of the impurities, and thereby the desired proteins can effectively and easily be purified.

According to the method of this invention using the removal agent containing a low molecular chitosan, the nucleic acids and/or endotoxin can effectively be removed from the liquid to be treated. When the removal agent of this invention is applied to a liquid containing proteins, the nucleic acids and/or endotoxin can be removed while the specific proteins remain in the solution, and hence, the steps in the procedure can be simplified. Besides, when the removal agent of this invention is applied to a cell extract in order to purify the proteins, the nucleic acids and/or endotoxin can effectively be removed by using only a small amount of the agent, and hence, further purification in the subsequent step can be effected with the minimum load. Furthermore, the removal agent of this invention can also be used for the removal of high viscous nucleic acids in the form of precipitate, which can subsequently be treated with a filter for sterilization, and further, it can easily be further purified by a conventional chromatography. The method of this invention is also advantageous in comparison with the known methods in the cost for apparatus, and hence, it is highly valuable from the industrial viewpoint, too.

This invention is illustrated by the following Preparations and Examples but should not be construed to be limited thereto.

PREPARATION 1

Preparation of low molecular chitosans:

Chitin prepared from exoskeletons of crabs is treated with NaOH to deacetylate to give a chitosan having a high molecular weight. The chitosan (30 g/l or 67 g/l) thus obtained is suspended in an aqueous NaOH solution (pH 11), and the solution is maintained at 70° C. To the solution is added $H_2O_2$ (0.088–14 g/l) with stirring, and the mixture is subjected to the reaction for 110 to 300 minutes, and the product is separated by filtration and then pulverized. The low molecular chitosans thus obtained (sample Nos. C-1 to C-9) are shown in Table 1 together with the physical properties thereof.

In Table 1, $H_2O_2$ is a 35% aqueous solution.

The intrinsic viscosity [$\eta$] was measured as follows.

To the sample was added the same weight amount of acetic acid to prepare an aqueous solution of the sample (0.2–10 g/dl). The solution was mixed with the same amount of 0.4M $CH_3COOH + 0.2M$ $CH_3COONa$ solution to prepare a sample solution for the measurement of $[\eta]$. The viscosity was measured with Ubbellohde viscometer (dilution type) at 30° C., wherein the sample solution was diluted with 0.2M $CH_3COOH + 0.1M$ $CH_3COONa$.

The colloid equivalent (C.E.) is shown by the value at pH 4.

TABLE 1

| Samples | Evaporated residue % (w/w) | 35% $H_2O_2$ (ml/l) | Time (minute) | $[\eta]$ (dl/g) | Colloid Eq. (meq/g of evaporated residue) |
|---|---|---|---|---|---|
| Chitosan having high mol. wt. | — | — | | 13.5 | 4.9 |
| Low mol. chitosan | | | | | |
| C-1 | 90.3 | 0.25 | 130 | 5.2 | 5.1 |
| C-2 | 89.8 | 1.0 | 110 | 3.1 | 5.0 |
| C-3 | 90.8 | 2.0 | 110 | 2.3 | 4.9 |
| C-4 | 88.0 | 4.0 | 120 | 1.7 | 5.0 |
| C-5 | 88.1 | 6.0 | 120 | 1.4 | 5.0 |
| C-6 | 89.7 | 10.0 | 130 | 0.68 | 4.8 |
| C-7 | 90.2 | 26.7 | 180 | 0.40 | 4.5 |
| C-8 | 91.5 | 33.3 | 300 | 0.38 | 4.3 |
| C-9 | 90.9 | 40.0 | 270 | 0.25 | 4.5 |

Among the above samples, chitosan having a high molecular weight has an extremely high viscosity and the upper limit of solubility in dilute HCl solution is 0.5% (pH 6), but on the other hand, in case of samples C-1 to C-5, 3% solution can be prepared, and in case of samples C-6 to C-8, 5% solution can be prepared, and further in case of sample C-9, 10% solution can be prepared.

An appropriate amount of the chitosan having a high molecular weight or the low molecular chitosans (C-1 to C-9) prepared above is dissolved in the same amount of dilute HCl and adjusted to pH 6.0-7.0 with NaOH to prepare sample solutions containing the chitosan having a high molecular weight or the low molecular chitosans, which are used in the Examples hereinafter.

PREPARATION 2

Preparation of cell extract containing human tumor necrosis factor (TNF) polypeptide:

In the same manner as described in European Patent Publication No. 155,549, Example 2-(2), *E. coli* HB101/pHTR-91 is cultured, which contains human TNF polypeptide in itself. The culture broth is centrifuged to harvest cells, and the cells are disrupted and then centrifuged to obtain a supernatant containing the human TNF polypeptide. The supernatant is used in the Examples hereinafter.

PREPARATION 3

Preparation of cell extract containing human interleukin 1 (IL-1) polypeptide:

In the same manner as described in European Patent Publication No. 188,920, Example 5-(2), *E. coli* HB101/pHLP-383 is cultured, which contains human IL-1 polypeptide in itself. The culture broth is centrifuged to harvest cells, and the cells are disrupted and then centrifuged to obtain a supernatant containing the human IL-1 polypeptide. The supernatant is filtered through a membrane for sterilization (Microflow ®, manufactured by Flow Labs., pore diameter: 0.2 $\mu$m) and the filtrate is used in Example 5 hereinafter.

REFERENCE EXAMPLE 1

Effect of chitosan having a high molecular weight for the removal of nucleic acids:

To the supernatant (2 ml) prepared in the above Preparation 2 was added an appropriate amount of 0.5% solution (pH 3) of chitosan having a high molecular weight and having an intrinsic viscosity $[\eta] = 13.5$ prepared in the above Preparation 1, and the mixture was stirred. The mixture was allowed to stand under ice cooling and centrifuged with a cooling centrifuge at 4° C., 3,000 r.p.m. for 10 minutes. The supernatant was used for the determination of nucleic acids (DNA, RNA) and proteins. The results are shown in Table 2.

TABLE 2

| Amount of chitosan (ml per 2 ml of supernatant) | Final concentration of chitosan % (w/v) | Total DNA amount (remaining rate) $\mu$g (%) | Total RNA amount (remaining rate) $\mu$g (%) | Total protein amount (remaining rate) mg (%) |
|---|---|---|---|---|
| 0 | 0 | 1100 (100) | 7670 (100) | 26.12 (100) |
| 0.5 | 0.1 | 900 (82) | 6400 (83) | 24.43 (94) |
| 1.0 | 0.17 | 620 (56) | 4330 (56) | 22.08 (85) |

As is shown in Table 2, when the 0.5% chitosan solution was added in an amount almost equal to or more than the volume of the supernatant, the removal effect of nucleic acids was observed, but an increase of the mixture volume was inevitable, and hence, it is not suitable for practical use.

EXAMPLE 1

Effect of low molecular chitosans (C-1 to C-6) for the removal of nucleic acids:

To the supernatant (2 ml) in different lot prepared in the above Preparation 2 was added an appropriate amount of each solution (pH 4) of low molecular chitosans (C-1 to C-6) prepared in the above Preparation 1 and the mixture was treated under the same conditions as described in the above Reference Example 1. The results are shown in Table 3 and Table 4.

TABLE 3

| Sample solution | Amount of low mol. chitosan (ml/2 ml supernatant) | Final concn. of low mol. chitosan % (w/v) | Total DNA amount (remaining rate) $\mu$g (%) | Total RNA amount (remaining rate) $\mu$g (%) | Total protein amount (remaining rate) mg (%) |
|---|---|---|---|---|---|
| None | 0 | 0 | 1340 (100) | 5940 (100) | 22.4 (100) |
| 3.3% C-1 | 0.4 | 0.83 | 14 (1) | 320 (5) | 14.0 (63) |
| 5% C-2 | 0.4 | 0.83 | <5 (<0.4) | <50 (<0.8) | 13.4 (60) |
| 5% C-3 | 0.3 | 0.65 | 18 (1) | <50 (<0.8) | 16.2 (72) |

TABLE 4

| Sample solution | Amount of low mol. chitosan (ml/2 ml supernatant) | Final concn. of low mol. chitosan % (w/v) | DNA amount (remaining rate) $\mu$g/ml (%) | RNA amount (remaining rate) $\mu$g/ml (%) | Protein amount (remaining rate) mg/ml (%) |
|---|---|---|---|---|---|
| None | 0 | 0 | 680 (100) | 3200 (100) | 13.51 (100) |
| 5% | 0.15 | 0.375 | 58 | 348 | 13.54 |

TABLE 4-continued

| Sample solution | Amount of low mol. chitosan (ml/2 ml) supernatant | Final concn. of low mol. chitosan % (w/v) | DNA amount (remaining rate) μg/ml (%) | RNA amount (remaining rate) μg/ml (%) | Protein amount (remaining rate) mg/ml (%) |
|---|---|---|---|---|---|
| C-4 |  |  | (9) | (11) | (100) |
| 5% C-5 | 0.15 | 0.375 | <5 (<0.7) | <50 (<2) | 7.76 (57) |
| 5% C-6 | 0.1 | 0.25 | <5 (<0.7) | <50 (<2) | 6.29 (47) |

EXAMPLE 2

Effect of low molecular chitosans (C-7 to C-9) for removal of nucleic acids and endotoxin:

The low molecular chitosans (C-7 to C-9) prepared in the above Preparation 1 were dissolved in dilute HCl and adjusted to pH 6 with 6N NaOH and adjusted the final concentration of the low molecular chitosan to 5%.

To the supernatant (2 ml) containing human TNF polypeptide prepared in the above Preparation 2 was added an appropriate amount of the solution of a low molecular chitosan prepared above, and the mixture was stirred. The mixture was allowed to stand for about 10 minutes under ice cooling and centrifuged with a cooling centrifuge at 4° C., 3000 r.p.m. for 10 minutes. The resulting supernatant was used for the determination of nucleic acids, endotoxin and for the assay of TNF titer. The results are shown in Table 5.

TABLE 5

| Sample solution | Amount of low mol. chitosan (ml/2 ml of supernatant) | Final concn. of low mol. chitosan % (w/v) | DNA amount (remaining rate) μg/ml (%) | RNA amount (remaining rate) μg/ml (%) | Endotoxin amount (remaining rate) ng/ml (%) | Titer of TNF (remaining rate) × $10^4$ IRU/ml (%) |
|---|---|---|---|---|---|---|
| none | 0 | 0 | 570 (100) | 2700 (100) | $1.4 \times 10^5$ (100) | 750 (100) |
| 5% C-7 | 0.1 | 0.25 | <5 (<0.9) | 120 (4) | $2.9 \times 10^2$ (0.2) | 650 (87) |
| 5% C-8 | 0.1 | 0.25 | 20 (4) | 220 (8) | $1.3 \times 10^3$ (0.9) | 720 (96) |
| 5% C-9 | 0.1 | 0.25 | <5 (<0.9) | 150 (6) | $2.7 \times 10^2$ (0.2) | 720 (96) |

EXAMPLE 3

Effect of the low molecular chitosan (C-9) for the removal of nucleic acids in various cell extracts:

Lyophilized cells (2.5 g) of *Bacillus subtilis* ATCC 6633, *Saccharomyces cerevisiae* or *Escherichia coli* K-12, or lyophilized cells (1.3 g) of *Pseudomonas fluorescens* ATCC 13430 was suspended in 20 mM Tris-HCl buffer (pH 7.5) (50 ml) and treated with ultrasonic (Tomy Seiko, Model UR-200P). The mixture was centrifuged with a cooling centrifuge at 4° C., 10,000 r.p.m. for 10 minutes. Each supernatant was used as *B. subtilis* extract, *S. cerevisiae* extract, *E. coli* extract, and *P. fluorescens* extract, respectively, in the experiments hereinafter.

HeLa cells (ATCC CCL2) was inoculated into Eagle's minimum essential medium containing 10% (v/v) fetal calf serum [cf. Paul, "Cell and Tissue Culture", E. & S. Livingstone Ltd. (1970)] and cultivated in 5% $CO_2$-air at 37° C. for 48 hours. The cells were treated with trypsin and centrifuged to harvest cells. The cells were resuspended in a physiological saline. The suspension of HeLa cells (10 ml, containing about $2 \times 10^7$ cells) was treated with ultrasonic (Tomy Seiko, Model UR-200P) to give HeLa cell extract which was used in the experiments hereinafter.

In case of the *B. subtilis* extract, *S. cerevisiae* extract or HeLa cell extract, to each extract (2 ml) was added TNF solution ($7 \times 10^7$ IRU/ml) (0.1 ml), and in case of *E. coli* extract or *P. fluorescens* extract, to each extract (2 ml) was added TNF solution ($1 \times 10^8$ IRU/ml) (0.1 ml). To the mixture was added an appropriate amount of a 5% solution (pH 6) of the low molecular chitosan (C-9), and the mixture was allowed to stand under ice cooling for about 10 minutes. The resulting mixture was centrifuged with a cooling centrifuge at 4° C., 3,000 r.p.m. for 10 minutes, and the supernatant was used for the determination of nucleic acids and for the assay of TNF titer. In the above experiment, the TNF solution was a human TNF polypeptide solution which was prepared by the method as disclosed in European Pat. Publication 155,549, Example 5.

The results are shown in Table 6. As is clear from the results, the low molecular chitosan of this invention showed excellent effect for the removal of nucleic acids from various cell extracts without loss of TNF titer in the supernatant.

TABLE 6

| Sample solution | Final concn. of low mol. chitosan % (w/v) | DNA amount (remaining rate) μg/ml (%) | RNA amount (remaining rate) μg/ml (%) | TNF titer (remaining rate) × $10^4$ IRU/ml (%) |
|---|---|---|---|---|
| B. subtilis extract | 0 | 710 (100) | 870 (100) | 340 (100) |
|  | 0.125 | 44 (6) | <50 (<6) | 320 (94) |
|  | 0.18 | 37 (5) | <50 (<6) | 320 (94) |
|  | 0.25 | <5 (<0.7) | <50 (<6) | 320 (94) |
| E. coli extract | 0 | 1410 (100) | 2460 (100) | 515 (100) |
|  | 0.125 | 1100 (78) | 1540 (63) | 498 (97) |
|  | 0.18 | 364 (26) | 735 (30) | — |
|  | 0.25 | 58 (4) | 137 (6) | 433 (84) |
| P. fluorescens extract | 0 | 968 (100) | 1770 (100) | 541 (100) |
|  | 0.125 | 26 (3) | 83 (5) | 484 (89) |
|  | 0.18 | 16 (2) | 62 (3) | 507 (94) |
|  | 0.25 | 6 (0.6) | 50 (3) | 466 (86) |
| S. cerevisiae extract | 0 | 52 (100) | 1170 (100) | 350 (100) |
|  | 0.125 | 8 (15) | 50 (4) | 350 (100) |
|  | 0.18 | 9 (17) | <50 (<4) | 310 (89) |
|  | 0.25 | 6 (12) | <50 (<4) | 320 (91) |
| HeLa cell extract | 0 | 95 (100) | 140 (100) | 310 (100) |
|  | 0.125 | 10 (11) | <50 (<36) | 310 (100) |
|  | 0.18 | 9 (9) | <50 (<36) | 310 (100) |
|  | 0.25 | 7 (7) | <50 (<36) | 280 (90) |

EXAMPLE 4

Effect of pH on the removal of nucleic acids and endotoxin by the low molecular chitosan (C-9):

To the supernatant containing human TNF polypeptide prepared in the above Preparation 2 was added 1M citric acid and the mixture was adjusted to pH 7 or pH 6, and thereto was added an appropriate amount of a 5% solution of the low molecular chitosan (C-9) (adjusted to pH 7 or pH 6). The mixture was stirred and allowed to stand under ice cooling for about 10 minutes and then centrifuged with a cooling centrifuge at 4° C., 3,000 r.p.m. for 10 minutes. The supernatant was used for the determination of nucleic acids, endotoxin and for the assay of TNF titer.

The results are shown in Table 7. As is clear from the results, the treatment with the low molecular chitosan solution adjusted to pH 6 showed more favorable effect of removal of nucleic acids and endotoxin than the case of the treatment with the low molecular chitosan solution adjusted to pH 7. Besides, when the treatment was repeated except using a low molecular chitosan solution adjusted to pH 5, the removal effect was more increased, but the TNF titer was unfavorably decreased.

tion adjusted to pH 7, and showed such a high remaining rate of interleukin 1 as 80% or more.

TABLE 8

| pH | Final concn. of low mol. chitosan % (w/v) | IL-1 amount (remaining rate) μg/ml (%) | Endotoxin amount (remaining rate) ng/ml (%) |
|---|---|---|---|
| 7 | 0 | 433 (100) | $8.49 \times 10^4$ (100) |
|   | 0.1 | 410 (95) | $8.66 \times 10^4$ (102) |
|   | 0.15 | 442 (102) | $6.20 \times 10^4$ (73) |
|   | 0.2 | 443 (102) | $1.32 \times 10^4$ (16) |
|   | 0.25 | 438 (101) | $1.10 \times 10^3$ (1) |
| 5 | 0 | 331 (76) | $3.10 \times 10^4$ (37) |
|   | 0.025 | 357 (82) | $3.50 \times 10^3$ (4) |
|   | 0.05 | 358 (83) | $1.14 \times 10^2$ (0.1) |
|   | 0.075 | 375 (87) | $2.49 \times 10$ (0.03) |
|   | 0.1 | 353 (82) | $2.09 \times 10$ (0.02) |

EXAMPLE 6

Effect of salt concentration on the effect of the removal of nucleic acids and endotoxin by the low molec-

TABLE 7

| pH | Final concn. of low mol. chitosan % (w/v) | Protein amount (remaining rate) mg/ml (%) | DNA amount (remaining rate) μg/ml (%) | RNA amount (remaining rate) μg/ml (%) | TNF titer (remaining rate) × $10^4$ IRU/ml (%) | Endotoxin amount (remaining rate) ng/ml (%) |
|---|---|---|---|---|---|---|
| 7 | 0 | 7.19 (100) | 644 (100) | 2570 (100) | 948 (100) | $2.57 \times 10^4$ (100) |
|   | 0.15 | 5.80 (81) | 312 (48) | 1290 (50) | 973 (103) | $1.68 \times 10^4$ (65) |
|   | 0.2 | 5.68 (79) | 72 (11) | 605 (24) | 897 (95) | $5.05 \times 10^3$ (20) |
|   | 0.25 | 5.13 (71) | 8 (1) | 204 (8) | 930 (98) | $2.44 \times 10^3$ (9) |
|   | 0.3 | 5.48 (76) | <5 (<0.6) | 209 (8) | 926 (98) | $7.54 \times 10^2$ (3) |
| 6 | 0 | 5.90 (82) | 620 (96) | 2460 (96) | 785 (83) | $4.18 \times 10^4$ (163) |
|   | 0.1 | 5.77 (80) | 360 (56) | 1140 (44) | 829 (87) | $2.43 \times 10^4$ (95) |
|   | 0.15 | 4.93 (69) | 84 (13) | 374 (15) | 778 (82) | $8.18 \times 10^3$ (32) |
|   | 0.2 | 5.07 (71) | 6 (0.9) | 159 (6) | 773 (82) | 121 (0.5) |
|   | 0.25 | 4.17 (58) | <5 (<0.6) | 151 (6) | 740 (78) | 57.3 (0.2) |

EXAMPLE 5

Effect of pH on the removal of endotoxin by the low molecular chitosan (C-9):

The filtrate containing human IL-1 polypeptide prepared in the above Preparation 3 was adjusted to pH 7 or pH 5 with 1M citric acid, and thereto was added an appropriate amount of a 5% solution of the low molecular chitosan (C-9) (which was adjusted to pH 7 or pH 5). The mixture was stirred and allowed to stand under ice cooling for about 10 minutes and then centrifuged with a cooling centrifuge at 4° C., 3,000 r.p.m. for 10 minutes. The supernatant was used for the determination of endotoxin and interleukin 1.

The results are shown in Table 8. As is clear from the results, when the treatment was done by the low molecular chitosan solution adjusted to pH 5, the effect of the removal of endotoxin was significantly more favorable than the case of using the low molecular chitosan soluular chitosan (C-9):

To the supernatant containing human TNF polypeptide (2 ml) prepared in the above Preparation 2 was added various concentrations of sodium chloride, and to each solution was added an appropriate amount of a 5% solution of the low molecular chitosan (C-9) (pH 6) so as to be the final concentration of the low molecular chitosan of 0.3%. The mixture was stirred and allowed to stand under ice cooling for about 10 minutes, and then centrifuged with a cooling centrifuge at 4° C., 3,000 r.p.m. for 10 minutes. The supernatant was used for the determination of nucleic acids and endotoxin and for the assay of TNF titer.

The results are shown in Table 9. As is clear from the results, when the concentration of sodium chloride was lower than 0.5 M, the desired effect of the removal of nucleic acids and/or endotoxin by the low molecular chitosan was sufficiently exhibited, but when the concentration of sodium chloride was over 0.5 M, there was tendency of decreasing of the removal effect.

TABLE 9

| Final concn. of sodium chloride M | Final concn. of low mol. chitosan % (w/v) | Protein amount (remaining rate) mg/ml (%) | DNA amount (remaining rate) μg/ml (%) | RNA amount (remaining rate) μg/ml (%) | TNF titer (remaining rate) × $10^4$ IRU/ml (%) | Endotoxin amount (remaining rate) ng/ml (%) |
|---|---|---|---|---|---|---|
| 0 | 0 | 7.39 (100) | 640 (100) | 1920 (100) | 1330 (100) | $2.36 \times 10^5$ (100) |
| 0 | 0.3 | 4.92 (67) | <5 (<0.6) | 87 (3) | 1330 (100) | $4.01 \times 10^2$ (0.2) |
| 0.05 | 0.3 | 5.07 (69) | 8 (1) | 106 (4) | 1300 (98) | $2.02 \times 10^2$ (0.09) |
| 0.1 | 0.3 | 5.28 (71) | 18 (3) | 115 (4) | 1310 (98) | $2.59 \times 10^2$ (0.1) |
| 0.2 | 0.3 | 5.60 (76) | 22 (3) | 124 (4) | 1310 (98) | $3.13 \times 10^2$ (0.1) |

TABLE 9-continued

| Final concn. of sodium chloride M | Final concn. of low mol. chitosan % (w/v) | Protein amount (remaining rate) mg/ml (%) | DNA amount (remaining rate) μg/ml (%) | RNA amount (remaining rate) μg/ml (%) | TNF titer (remaining rate) × 10⁴ IRU/ml (%) | Endotoxin amount (remaining rate) ng/ml (%) |
|---|---|---|---|---|---|---|
| 0.5 | 0.3 | 6.27 (85) | 44 (7) | 217 (7) | 1150 (86) | $6.00 \times 10^3$ (3) |
| 1.0 | 0.3 | 5.28 (71) | 176 (28) | 389 (13) | 1210 (91) | $3.24 \times 10^4$ (14) |

EXAMPLE 7

Effect of the low molecular chitosan (C-9) in solutions containing proteins having different isoelectric point:

Each protein having different isoelectric point was dissolved in 20 mM Tris-HCl buffer (pH 7.5), and thereto was added an appropriate amount of a 5% solution of the low molecular chitosan (C-9) (pH 6) under ice cooling, and the mixture was allowed to stand under ice cooling for about 10 minutes, and then centrifuged at 4° C., 3,000 r.p.m. for 10 minutes. The concentration of proteins in the supernatant was measured. The results are shown in Table 10.

TABLE 10

| Proteins | | | Concn. of proteins (remaining rate) mg/ml (%) | |
|---|---|---|---|---|
| | Isoelectric | Molecular weight | Final concn. of low mol. chitosan | |
| Kind (origin) | point | (× 10³) | 0% | 0.25% |
| Pepsin (pig gastric mucosa) | <1 | 33–35 | 3.7 (100) | 0.8 (22) |
| Fetuin (bovine serum) | 3.2–3.8 | 46–50 | 24.7 (100) | 20.8 (84) |
| Albumin (egg white) | 4.6 | 45 | 4.9 (100) | 3.6 (73) |
| Albumin (human serum) | 4.7–5.2 | 66 | 7.2 (100) | 6.8 (94) |
| α-Amylase (B. subtilis) | 5.5 | 42–49 | 4.5 (100) | 4.4 (98) |
| β-Amylase (barley) | 6.0 | 45–50 | 2.9 (100) | 2.5 (86) |
| Hemoglobin (bovine red blood cell) | 6.8–7.0 | 65 | 6.7 (100) | 6.6 (99) |
| α-Chymotrypsinogen A (bovine pancreas) | 9.5 | 25.7 | 4.6 (100) | 4.5 (98) |
| Cytochrome C (horse heart) | 10.1 | 12.4 | 8.1 (100) | 8.1 (100) |
| Trypsin (boviine pancreas) | 10.1–10.8 | 23 | 2.0 (100) | 2.0 (100) |
| Lysozyme (egg white) | 11.0–11.4 | 14.3 | 5.9 (100) | 5.6 (95) |

EXAMPLE 8

Effect of the low molecular chitosan (C-9) for the removal of nucleic acids and endotoxin in E. coli strain B extracts containing various proteins:

Lyophylized cells (2.5 g) of E. coli strain B (ATCC 11303) was suspended in 20 mM Tris-HCl buffer (pH 7.5) (50 ml), and the mixture was treated with ultrasonic (Tomy Seiko, Model UP-200R), and then centrifuged with a cooling centrifuge at 4° C., 10,000 r.p.m. for 10 minutes. The resulting supernatant was used as E. coli strain B extract hereinafter.

To the E. coli strain B extract (2 ml) was added a peptide (insulin or human growth hormone), an enzyme protein (pepsin or trypsin) or a protein (human serum albumin) in 20 mM Tris-HCl buffer (pH 7.5).

Separately, the low molecular chitosan (C-9) was dissolved in a dilute acetic acid and the solution was adjusted to pH 6 with 6N NaOH, and then the final concentration of the low molecular chitosan was adjusted to 5%.

To the E. coli strain B extract containing various peptides or proteins (2 ml) as prepared above was added the 5% solution of the low molecular chitosan (C-9) adjusted to pH 6 as above in an amount of 0, 50, 75 or 100 μl, and the mixture was stirred and allowed to stand under ice cooling for about 10 minutes and then centrifuged with a cooling centrifuge at 4° C., 3,000 r.p.m. for 10 minutes. The supernatant was used for the determination of nucleic acids (DNA, RNA), endotoxin and the peptides or proteins added previously to the E. coli strain B extract.

The results are shown in Table 11. As is clear from the results in Table 11, the peptides and proteins added previously to the E. coli strain B extract were almost remained in the supernatant except pepsin having a lower isoelectric point.

TABLE 11

| Additives | Final concn. of low mol. chitosan % (w/v) | DNA amount (remaining rate) μg/ml (%) | RNA amount (remaining rate) μg/ml (%) | Endotoxin amount (remaining rate) ng/ml (%) | Concentration of additive (remaining rate) (%) |
|---|---|---|---|---|---|
| Pepsin (pig gastric mucosa) (Isoelectric point: <1) | 0 | 80 (100) | 840 (100) | $1.1 \times 10^6$ (100) | $371 \times 10^3$ PU Hb/ml (100) |
| | 0.125 | <5 (<6) | <50 (<6) | $1.0 \times 10^3$ (0.1) | $16 \times 10^3$ Hb/ml (4) |
| | 0.18 | <5 (<6) | <50 (<6) | $1.1 \times 10^2$ (0.01) | $2 \times 10^3$ Hb/ml (0.5) |
| | 0.25 | <5 (<6) | <50 (<6) | $6.7 \times 10$ (0.007) | 0 Hb/ml (0) |
| Albumin (human serum) (Isoelectric point: 4.7–5.2) | 0 | 38 (100) | 890 (100) | $1.1 \times 10^6$ (100) | 8.4 mg/ml (100) |
| | 0.125 | <5 (<13) | 60 (7) | $1.2 \times 10^3$ (0.1) | 8.4 mg/ml (100) |
| | 0.18 | 5 (13) | 60 (7) | $1.9 \times 10^2$ (0.02) | 8.4 mg/ml (100) |
| | 0.25 | <5 (<13) | 57 (6) | $1.1 \times 10^2$ (0.01) | 8.4 mg/ml (100) |
| Human growth hormone (Isoelectric | 0 | 82 (100) | 960 (100) | $1.1 \times 10^6$ (100) | 8.3 ng/ml (100) |
| | 0.125 | <5 (<6) | 56 (6) | $3.1 \times 10^2$ (0.03) | 7.8 ng/ml (94) |
| | 0.18 | <5 (<6) | 60 (6) | $3.1 \times (0.003)$ | 7.6 ng/ml (92) |

TABLE 11-continued

| Additives | Final concn. of low mol. chitosan % (w/v) | DNA amount (remaining rate) μg/ml (%) | RNA amount (remaining rate) μg/ml (%) | Endotoxin amount (remaining rate) ng/ml (%) | Concentration of additive (remaining rate) (%) |
|---|---|---|---|---|---|
| point: 4.9–5.2) | 0.25 | <5 (<6) | 60 (6) | $2.1 \times 10$ (0.002) | 8.3 ng/ml (100) |
| Insulin | 0 | 80 (100) | 740 (100) | $8.2 \times 10^5$ (100) | 58.8 mU/ml (100) |
| (bovine) | 0.125 | <5 (<6) | <50 (<7) | $1.3 \times 10^3$ (0.2) | 58.8 mU/ml (100) |
| Isoelectric | 0.18 | <5 (<6) | <50 (<7) | $1.0 \times 10^2$ (0.01) | 50.1 mU/ml (85) |
| point: 5.3–5.8) | 0.25 | <5 (<6) | <50 (<7) | $2.7 \times 10$ (0.003) | 43.5 mU/ml (74) |
| Trypsin | 0 | 86 (100) | 740 (100) | $1.3 \times 10^6$ (100) | $149 \times 10^3$ TU Hb/ml (100) |
| (bovine pancreas) | 0.125 | <5 (<6) | <50 (<7) | $3.6 \times 10^2$ (0.03) | $105 \times 10^3$ Hb/ml (70) |
| (Isoelectric | 0.18 | <5 (<6) | <50 (<7) | $3.1 \times 10^2$ (0.02) | $135 \times 10^3$ Hb/ml (91) |
| point: 10.1–10.8) | 0.25 | <5 (<6) | <50 (<7) | $3.5 \times 10^2$ (0.03) | $143 \times 10^3$ Hb/ml (96) |

EXAMPLE 9

Recovery of nucleic acids from the precipitate formed by treatment with the low molecular chitosan (C-9):

To each 2 ml of E. coli (HB101/pHTR-91) extract containing human TNF polypeptide which was prepared in the above Preparation 2, the E. coli K-12 extract which was prepared in the above Example 3, or P. fluorescens (ATCC 13430) extract which was prepared in the above Example 3 was added 120 μl of a 5% solution of the low molecular chitosan (C-9) (pH 6), and the mixture was stirred and allowed to stand under ice cooling for about 10 minutes and then centrifuged with a cooling centrifuge at 4° C., 3,000 r.p.m. for 10 minutes, by which the supernatant*) and the precipitate**) were separated. The precipitate was resuspended in 20 mM Tris-HCl buffer (pH 7.5) (2 ml), and the mixture was centrifuged at 4° C., 3,000 r.p.m. for 10 minutes and then extracted with 0.01N NaOH (2 ml) or with 0.01N NaOH containing 1M NaCl (2 ml). The insoluble materials were removed off by centrifuge, and the amount of nucleic acids in the solution was measured. Besides the amount of nucleic acids in the above cell extract and the supernatant*) was also measured.

The results are shown in Table 12. As is clear from the results, when the cell extract was treated with the low molecular chitosan (C-9), the nucleic acids contained in the solution was effectively separated and recovered.

TABLE 12

| Samples | DNA amount (recovery rate) μg/ml (%) | RNA amount (recovery rate) μg/ml (%) |
|---|---|---|
| E. coli K-12 extract | 1300 (100) | 1810 (100) |
| Supernatant* | <5 (<0.04) | 52 (3) |
| Precipitate** extracted with | | |
| 0.01N NaOH | 1160 (89) | 1690 (93) |
| 1M NaCl—0.01N NaOH | 1130 (87) | 1500 (83) |
| E. coli HB101/pHTR-91 extract | 670 (100) | 2370 (100) |
| Supernatant* | 0 (0) | <50 (<2) |
| Precipitate** extracted with | | |
| 0.01N NaOH | 530 (79) | 1590 (67) |
| 1M NaCl—0.01N NaOH | 560 (83) | 2060 (87) |
| P. fluorescens extract | 972 (100) | 1760 (100) |
| Supernatant* | <5 (<0.5) | <50 (<3) |
| Precipitate** extracted with | | |
| 0.01N NaOH | 810 (83) | 1480 (84) |
| 1M NaCl—0.01N NaOH | 772 (79) | 1280 (73) |

As is clear from the above Examples, by the treatment with the low molecular chitosans, the nucleic acids and/or endotoxin contained in various materials of organisms such as cell extracts can effectively be removed, and particularly, the desired proteins and peptides having an isoelectric point of not less than 3 can advantageously be recovered. Besides, the nucleic acids and/or endotoxin can also be recovered at a useful substance.

In the above Examples, various analytical and determination methods were carried out in the following manner:

(1) Quantitative determination of protein:

It was measured by UV method [cf. Methods in Enzymology, Vol. 3, page 451 (1957), Acedemic Press], or by a colorimetry using Coomassie Brilliant Blue G250 (Bio-Rad Protein Assay Kit, manufactured by Bio-Rad, using bovine serum albumin as a standard protein).

(2) Quantitative determination of DNA:

It was measured by a fluorimetry using diaminobenzoic acid [cf. Seikakagu Jikken Koza (Series of Biochemical Experiments, No. 2, Chemistry of Nucleic acid I, Separation and Purification, page 5 (1975), Ed. by The Biochemical Society of Japan, issued by Tokyo Kagaku Dojin].

(3) Quantitative determination of RNA:

It was measured by a pentose determination method using orcinol-iron-hydrochloric acid [cf. Tamio Yamakawa, Ikagaku Jikken Koza (Medical Chemistry Experiment), Vol. 1, A, page 55 (1971), issued by Nakayama Shoten].

(4) Quantitative determination of endotoxin:

It was measured by using Pyrodick Kit (manufactured by Seikagaku Kogyo K.K.).

(5) Measurement of titer of TNF:

It was measured by a method used for kill of tumor cell in vitro or by an enzyme immunoassay. The former was carried out by the method disclosed in European Pat. Publication No. 155,549, pages 28–29. The latter was carried out by a method comprising competitively reacting β-galactosidase-labelled TNF and a TNF test sample with anti-TNF rabbit serum, separating the bound material (B) and the free material (F) by using a second antibody, coloring the β-galactosidase in the B fraction by reacting it with a coloring substrate, and measuring the TNF titer in the test sample by a colorimetry. The titer was expressed by IRU (Immuno reactive unit)/ml.

(6) Quantitative determination of interleukin 1:

It was measured by an enzyme immunoassay (sandwich method). That is, the antigen (IL-1) was specifically reacted with an antibody immobilized onto a plate, and the antigen bound to the immobilized antibody was reacted with an enzyme-labelled antibody to prepare a sandwich bound product: immobilized antibody-antigen-enzyme-labelled antibody. To the bound product was added a substrate solution, whereby they were subjected to an enzymatic reaction to make color. The degree of coloring is proportionate to the amount of the bound antigen, and hence, the amount of the antigen can be determined by measuring the absorbance of the reaction mixture. The titer was expressed by μg/ml compared with that of the standard IL-1.

(7) Measurement of titer of insulin:

It was measured by using Insulin RIA Kit (manufactured by Dainabot).

(8) Measurement of titer of growth hormone:

It was measured by using Human Growth Hormone RIA Kit (manufactured by Dainabot).

(9) Measurement of titer of pepsin:

It was measured by the method of W. Rick [cf. Methods of Enzymatic Analysis 2nd ed. by Bergmeyer, Acedemic Press, N.Y. (1965), 820–823] wherein bovine hemoglobin was used as a substrate.

(10) Measurement of titer of trypsin:

It was measured by the method of W. Rick [cf. Methods of Enzymatic Analysis 2nd ed. by Bergmeyer, Acedemic Press, N.Y. (1965), 808–811] wherein bovine hemoglobin was used as a substrate.

(11) Quantitative determination of human serum albumin:

It was measured by the method of F. L. Rodkey [cf. Clin. Chem., 11, 478–487 (1965)].

What is claimed is:

1. A method for the removal of nucleic acids and endotoxin from a liquid containing same and proteins which comprises adding sufficient amount of a low molecular weight chitosan having an intrinsic viscosity of 0.01 to 5 dl/g into the liquid to precipitate the nucleic acids and endotoxin present in the liquid and separating off said precipitate, thereby retaining a substantial portion of the proteins in said liquid.

2. The method according to claim 1, wherein the chitosan having a low molecular weight has a colloid equivalent of not lower than 2 meq/g of evaporated residue at pH 4.

3. The method according to claim 1, wherein the chitosan having a low molecular weight has an intrinsic viscosity of 0.2 to 1 (dl/g) and a colloid equivalent of not less than 4 meq/g of evaporated residue at pH 4.

4. The method according to claim 1, wherein said liquid additionally contains proteins having an isoelectric point of not less than 3.

5. The method according to claim 4, wherein the protein is human tumor necrosis factor.

6. The method according to claim 4, wherein the protein is human interleukin 1.

7. The method according to claim 1, wherein the liquid contains a cell extract obtained by disruption of cells of microorganisms or of animal or plant tissue.

* * * * *

UNITED STATES PATENT AND TRADEMARK OFFICE
CERTIFICATE OF CORRECTION

PATENT NO. : 4,885,168

DATED : December 5, 1989

INVENTOR(S) : Masanori Hashimoto, et al.

It is certified that error appears in the above-identified patent and that said Letters Patent is hereby corrected as shown below:

Column 1, line 60: "or a" should read as --or by a--

Column 14, line 68: "3.1X (0.003)" should read as --3.1X10 (0.003)--

Column 15, line 37: "Besides" should read as --Besides,--

Column 16, line 22: "at a" should read as --as a--

Column 16, line 36: "Experiments," should read as --Experiments),--

Signed and Sealed this

Twenty-sixth Day of March, 1991

Attest:

HARRY F. MANBECK, JR.

Attesting Officer      Commissioner of Patents and Trademarks